United States Patent
Itoh et al.

(10) Patent No.: US 11,440,920 B2
(45) Date of Patent: Sep. 13, 2022

(54) CHEMICAL METHOD OF PRODUCING SMTP GROUPS OR SMTP-7 AND INTERMEDIATES USED IN THE METHOD

(71) Applicant: Showa University, Tokyo (JP)

(72) Inventors: Takashi Itoh, Tokyo (JP); Kazuhiro Nagata, Tokyo (JP); Takuya Kanemitsu, Tokyo (JP); Michiko Miyazaki, Tokyo (JP); Yuichiro Tomisawa, Tokyo (JP); Misa Mori, Tokyo (JP)

(73) Assignee: SHOWA UNIVERSITY, Tokyo (JP)

( * ) Notice: Subject to any disclaimer, the term of this patent is extended or adjusted under 35 U.S.C. 154(b) by 0 days.

(21) Appl. No.: 16/671,545

(22) Filed: Nov. 1, 2019

(65) Prior Publication Data

US 2020/0140450 A1  May 7, 2020

(30) Foreign Application Priority Data

Nov. 2, 2018 (JP) .............................. JP2018-207794

(51) Int. Cl.
| | | |
|---|---|---|
| *C07D 493/04* | (2006.01) | |
| *C07D 311/58* | (2006.01) | |
| *C07C 67/30* | (2006.01) | |
| *C07C 67/31* | (2006.01) | |

(52) U.S. Cl.
CPC ............ *C07D 493/04* (2013.01); *C07C 67/30* (2013.01); *C07C 67/31* (2013.01); *C07D 311/58* (2013.01)

(58) Field of Classification Search
CPC .................................................. C07D 493/04
See application file for complete search history.

(56) References Cited

U.S. PATENT DOCUMENTS

| | | |
|---|---|---|
| 2009/0216028 A1 | 8/2009 | Hasumi et al. |
| 2012/0100579 A1 | 4/2012 | Hasumi et al. |
| 2012/0135996 A1 | 5/2012 | Honda et al. |
| 2015/0025251 A1 | 1/2015 | Hasumi et al. |

FOREIGN PATENT DOCUMENTS

| | | |
|---|---|---|
| GB | 2 318 117 | 4/1998 |
| JP | 5-176782 | 7/1993 |
| JP | 4257026 | 2/2009 |
| WO | 98/56940 | 12/1998 |
| WO | 2007/111203 | 10/2007 |
| WO | 2010/110026 | 9/2010 |
| WO | 2011/004620 | 1/2011 |
| WO | 2012/115209 | 8/2012 |
| WO | 2013/129661 | 9/2013 |

OTHER PUBLICATIONS

Singh, M., et al. "Synthetic Studies towards NG-121: Diastereoselective Synthesis of NG-121 Methyl Ether." Synthesis. (2012), vol. 44, pp. 3797-3804. (Year: 2012).*

Hasumi et al., "Small-molecule modulators of zymogen activation in the fibrinolytic and coagulation systems", FEBS Journal, 277: 3675-3687 (2010).

Nishimura et al., "Pre-SMTP, a key precursor for the biosynthesis of the SMTP plasminogen modulators", Journal of Antibiotics, 65: 483-485 (2012).

Mori et al., "Synthetic study of antioxidants with dihydropyran skeleton", with English language translation; oral presentation 29K-pm16S at the 136th Annual Meeting of the Pharmaceutical Society of Japan, Mar. 29, 2016 held at PACIFICO Yokohama (Conference Center), Yokohama, Japan.

Hasegawa et al., "Structure-activity relationships of 11 new congeners of the SMTP plasminogen modulator", Journal of Antibiotics, 63: 589-593 (2010).

Koide et al., "A new series of the SMTP plasminogen modulator with a phenylglycine-based side chain", Journal of Antibiotics, 65:91-93 (2012).

Koide et al., "A new series of the SMTP plasminogen modulators with a phenylamine-based side chain", Journal of Antibiotics, 65: 361-367 (2012).

Otake et al., "Isoprene Side-chain of SMTP is Essential for Soluble Epoxide Hydrolase Inhibition and Cellular Localization", Natural Products Communications, 11: 223-227 (2016).

Notice of Reasons for Refusal dated May 24, 2022 in Japanese Application No. 2018-207794 with English translation thereof.

(Continued)

*Primary Examiner* — John S Kenyon
(74) *Attorney, Agent, or Firm* — Wenderoth, Lind & Ponack, L.L.P.

(57) ABSTRACT

The present invention provides a compound having a dihydropyran structure, a method of producing a compound having a dihydropyran structure, a method of producing Pre-SMTP, a method of producing a group of SMTPs, and a pharmaceutical composition. The compound having a dihydropyran structure can be a useful intermediate in the chemically producing a group of Pre-SMTP and SMTP. Specifically, the compound having a dihydropyran structure is represented by the following formula (1), wherein: $R_3Si$ is a silyl group selected from TMS: trimethylsilyl, TES: triethysilyl, TBS (TBDMS): tert-butyldimethylsil, TIPS: triisopropylsilyl, TBDPS: tert-butyldiphenylsilyl, X is selected from COOH, CHO, and $-CH=C(CH_3)-(CH_2)_2-CH=C(CH_3)_2$.

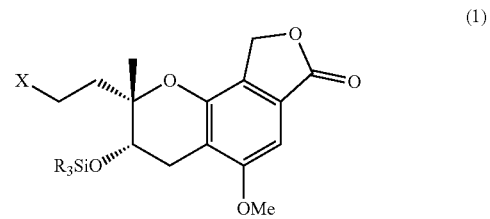

(1)

7 Claims, 1 Drawing Sheet

(56) References Cited

OTHER PUBLICATIONS

Matsumoto, Naoki et al., "Structure-activity relationships of the plasminogen modulator SMTP with respect to the inhibition of soluble epoxide hydrolase", Journal of Antibiotics, 2015, vol. 68, pp. 685-690.
Hu, Weimin et al., "SMIP-4D, -5D, -6D, -7D and -8D, a New Series of the Non-lysine-analog Plasminogen Modulators with a D-Amino Acid Moiety", Journal of Antibiotics, 2003, vol. 56, pp. 832-837.
Chen, Lingling et al., Bioactive natural products from the marine-derived Penicillium brevicompactum OUCMDZ-4920, Chinese Journal of Organic Chemistry, 2017, vol. 37, pp. 2752-2762.

* cited by examiner

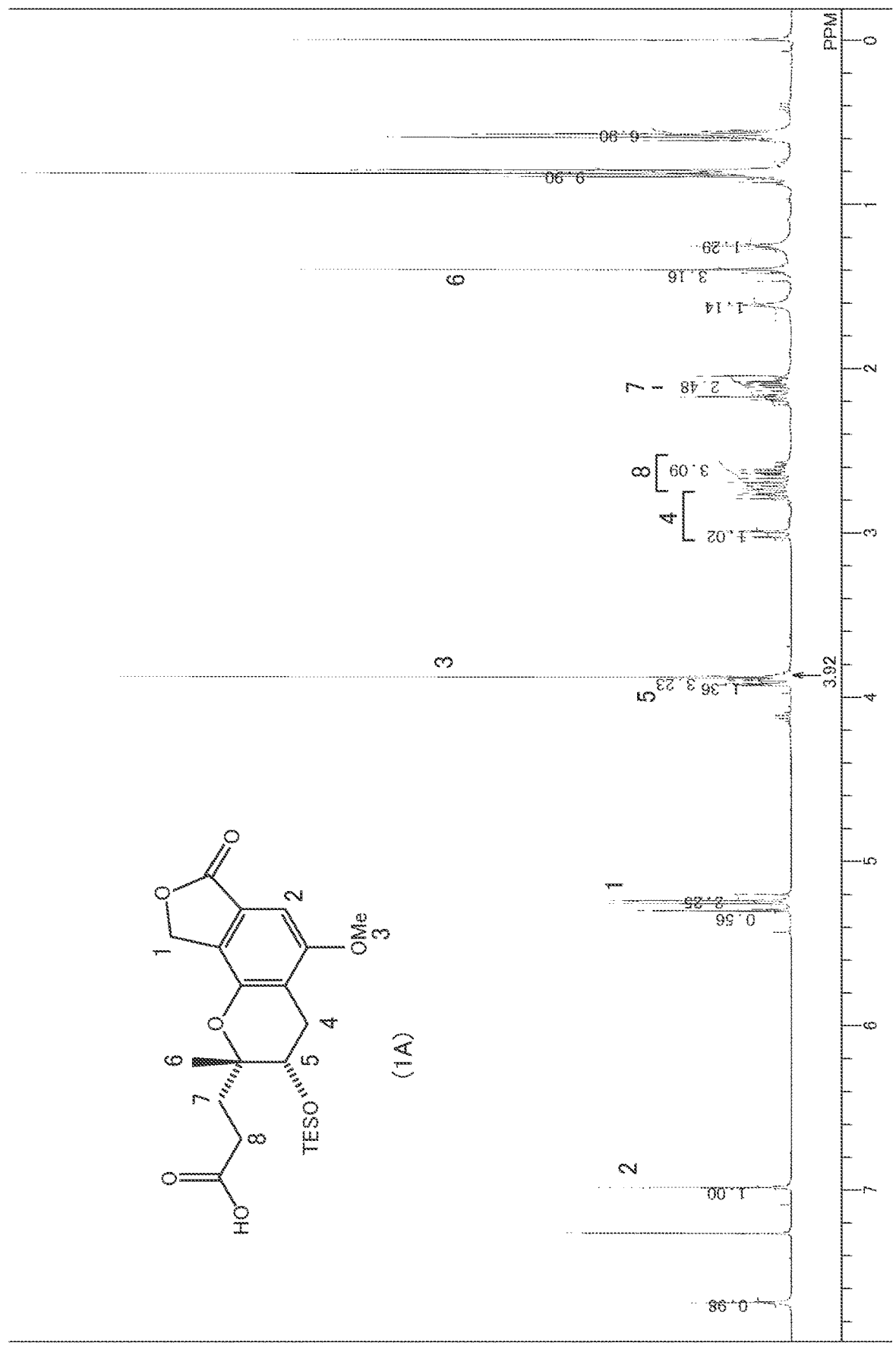

CHEMICAL METHOD OF PRODUCING SMTP GROUPS OR SMTP-7 AND INTERMEDIATES USED IN THE METHOD

STATEMENT REGARDING PRIOR DISCLOSURE BY INVENTOR

The content of the present application has been disclosed by the inventors of the present application. The first disclosure was made during 138$^{th}$ Annual Meeting of the Pharmaceutical Society of Japan on Feb. 1, 2018. The disclosure shall however be disqualified as prior art under 35 U.S.C. 102(b)(1).

CROSS-REFERENCE TO RELATED APPLICATION

The present application is based on and claims a priority benefit of Japanese patent application No. 2018-207794 filed on Nov. 2, 2018, the disclosure of which is hereby incorporated herein by reference in its entirety.

TECHNICAL FIELD

The present disclosure relates to the chemical method of producing SMTP groups or SMTP-7 and intermediates used in the methods.

BACKGROUND

Since the discovery of antibiotics, microbial secondary metabolism has been recognized as a treasure chest of diverse compounds, and a vast number of compounds have been isolated from it. However, some compounds are chemically synthesized more efficiently than they are isolated from microorganisms.

*Stachybotrys Microspora* Triprenyl phenol (SMTP) is a generic name for a group of novel triprenyl phenols produced by the fungus *S. microspora* and consists of a chromanlactam structure, isoprene side chains and N-linked side chains. To date, more than 50 homologues with different N-bond side chain structures and 8 homologues with different isoprene side chain structures have been identified (for example, see K. Hasumi, S. Yamamichi & T Harada: *FEBS J.*, 277, 3675 (2010). K. Hasegawa, H. Koide, W Hu, N. Nishimura, R. Narasaki, Y Kitano & K. Hasumi: *J. Antibiot.*, 63, 589 (2010). H. Koide, R. Narasaki, K. Hasegawa, N. Nishimura & K. Hasumi: *J. Antibiot.*, 65, 91 (2012). H. Koide, K. Hasegawa, N. Nishimura, R. Narasaki & K. Hasumi: *J. Antibiot.*, 65, 361 (2012). S. Otake, N. Ogawa, Y Kitano, K. Hasumi & E. Suzuki: *Nat. Prod. Commun.*, 11, 223 (2016)). One of its homologs, SMTP-7, is widely known to be effective in a cerebral infarction model caused by thrombus or embolism (For example, see WO2010/110026A1 (Patent Document 1)).

SMTP-7 is an example of a compound comprising a triprenyl phenol skeleton. In addition to SMTP-7, a compound comprising a triprenyl phenol skeleton comprising not only a dissolving action but also an antioxidant action and an anti-inflammatory action has been reported (for example, see WO98/56940A1 (Patent Document 2)). For example, JP4257026B1 (Patent Document 3) discloses a selective production method of a compound comprising a triprenyl phenol skeleton in a short time by a culture method in which an amino acid, amino alcohol, or the like corresponding to a substituent is added at the initial stage of cultivation of a filamentous fungus, such as immediately after the start of cultivation.

WO2007/111203A1 (Patent Document 4) discloses a compound comprising a triprenyl phenol skeleton capable of exerting a high thrombolysis promoting action with a low molecular weight and a method of producing the same. The three types of production methods of general formulas (I) to (III) disclosed in Patent Document 4 are all production methods for culturing and isolating filamentous fungi, and are compounds comprising a highly active triprenyl phenol skeleton obtained based on the general formulas (I) to (III).

However, Patent Documents 1 to 4 and the conventional production methods do not report an efficient production method for Pre-SMTP, which is a precursor of SMTP groups. Pre-SMTP has an o-phthalaldehyde partial structure, which can react with amine compounds to afford a phthalimidine structure as that present in SMTPs.

Furthermore, the microbial production of SMTP congeners is difficult to adapt certain amines, because of the problems with cellular uptake issues. For example, congeners with L-glutamine and L-glutamic acid as the N-linked side chain have not been produced through the precursor amine-feeding method. However, the nonenzymatic reaction between the precursor Pre-SMTP and these amines afforded congeners with an expected side chain, SMTP-54 and SMTP-55, respectively. That is, it is possible to obtain many highly active compounds comprising a triprenyl phenol skeleton from Pre-SMTP.

As described above, since a compound comprising a triprenyl phenol skeleton exhibits various activities depending on its steric structure and substituents, there is a strong demand for a production method that is highly useful, inexpensive and stable. Conventionally, these compounds comprising a triprenyl phenol skeleton are produced by filamentous fungi together with many analogs, so that the yield is relatively poor, and many chromatographic operations are required for purification, and obtain to a large amount of preparation is difficult. Therefore, various attempts have been made to efficiently isolate a large amount of each compound comprising a triprenyl phenol skeleton, but only a production method using filamentous fungi has been reported. In Patent Document 1, the amount of isolation has been improved compared to before, but it is still produced by culturing a production bacterium such as a bacterium belonging to the *Stachybotrys* fungus or *Stachybotrys microspora* IFO30018, and the yield is low. In Patent Document 3, the compounds obtained selectively are limited to compounds comprising a triprenyl phenol skeleton represented by three types of general formulas (I) to (III). In the prior art, Pre-SMTP is known to be separated from the fungus *S. microspora* (for example, see Y. Nishimura, E. Suzuki, K. Hasegawa, N. Nishimura, Y Kitano & K. Hasumi: *J. Antibiot.*, 65, 483 (2012)). Therefore, the production method by chemical synthesis has not been reported yet.

SUMMARY

The present disclosure has been made in view of the above circumstances, and becomes a useful intermediate when chemically producing a group of Pre-SMTP and SMTP, particularly when chemically producing SMTP-7. It is an object of the present disclosure to provide a compound having a dihydropyran structure, a method of producing a compound having a dihydropyran structure, a method of producing Pre-SMTP, a method of producing a group of SMTPs, and a pharmaceutical composition.

In light of the above prior art, the present inventors have made extensive studies with the object of developing a chemical production method of SMTP groups or SMTP-7, and as a result, commercially available methyl 3,5-dimethoxybenzoate was used as a starting material. We have succeeded in synthesizing intermediates that enable the production of SMTP groups or SMTP-7 by chemical production methods.

The present inventors considered the chemical decomposition reaction of SMTP-7, which will be described later, and in particular, it is considered that when it is decomposed by the chemical method of Pre-SMTP, it is converted to a compound having a dihydropyran structure. As a result, the present disclosure was completed.

That is, the present disclosure is as shown in the following (a) to (p).

(a) A compound having a dihydropyran structure represented by the following formula (1).

[Chem. 1]

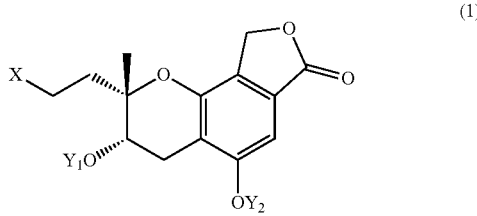

wherein $Y_1$ and $Y_2$ are protecting group, and X is selected from COOH, CHO, and —CH=C(CH$_3$)—(CH$_2$)$_2$—CH=C(CH$_3$)$_2$.

According to the present disclosure present disclosure, it is provided a microorganism-produced antioxidant having a dihydropyran structure that can be an intermediate useful for the chemical production step of a group of SMTP and Pre-SMTP, particularly for the chemical production step of SMTP-7. In addition, by including the microorganism-produced antioxidant or including the production step thereof, the production method capable of producing a compound comprising a highly active triprenyl phenol skeleton by a chemical production method can be provided.

BRIEF DESCRIPTION OF DRAWINGS

FIG. 1 shows a $^1$H NMR signal of a compound having a dihydropyran structure represented by the formula (1A) as an example of a compound having a dihydropyran structure, which is a feature of the present disclosure.

EMBODIMENTS

Embodiments according to the present disclosure will be described below.

First Embodiment

Embodiments according to the present disclosure will be described below.

First Embodiment

The compounds having a dihydropyran structure according to this embodiment is represented as the following formula (1).

[Chem. 2]

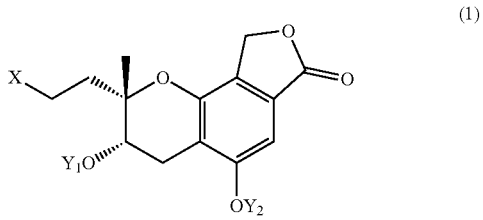

In formula (1), $Y_1$ and $Y_2$ are protecting groups, and X is selected from COOH, CHO, and —CH=C(CH$_3$)—(CH$_2$)$_2$—CH=C(CH$_3$)$_2$.

Hereinafter, although an example of the production method of the compounds which have the dihydropyran structure represented by the above formula (1) is demonstrated, the production method of the compounds which have the dihydropyran structure represented by the above formula (1) are not limited to the following example.

In this embodiment, $^1$H NMR of the compounds are measured with a JEOL JNM AL-400 type instrument. MS are measured with a JEOL JMS-MS700V type instruments and all use FAB method unless otherwise noted. All solvents are freshly distilled before use, and any anhydrous solvent used is obtained in a drying step according to standard methods. Unless otherwise stated, all reactions are carried out under nitrogen protection, followed by TLC, washed with saturated aqueous sodium chloride solution and dried over anhydrous sodium sulfate during the post processing. Unless otherwise stated, for purification of products, silica gel (200-300 mesh) column chromatography is used.

In this embodiment, suitable protecting groups for OH are well known for a skill person in the art. A general review of protecting groups in organic chemistry is provided by Peter G. M Wuts in Greene's Protective Groups in Organic Synthesis, 5$^{th}$ Ed. Wiley-Interscience, and by Kocienski P J in Protecting Groups, 3$^{th}$ Ed. Georg Thieme Verlag.

Examples of such protected OH include silyl ethers, ethers, esters, sulfonates, sulfenates and sulfinates, carbonates and carbamates. In the case of silyl ethers the protecting group for the OH can be selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis (t-butyl)-1-pyrenylmethoxysilyl, tris (trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of ethers the protecting group for the OH can be selected from methyl, methoxymethyl, methylthiomethyl, (phenyldimethyl silyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethyl silyl)ethoxymethyl, menthoxymethyl, o-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S, S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethyl silylethyl, 2-(benzylthio)ethyl, 2-phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methyl sulfinyl)benzyl, p-siletanylbenzyl, 4-acetoxybenzyl, 4-(2-trimethylsilyl)ethoxymethoxybenzyl, 2-naphthylmethyl, 2-picolyl, 2-picolyl, 3-methyl-2-picolyl N-oxido, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, .alpha.-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl) carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis(ethoxycarbonyl)-[1,3]-dioxolan-2-yl, benzisothiazolyl S,S-dioxido. In the case of silyl ethers the protecting group for the OH can be selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethyl silyl, (2-hydroxystyryl)diisopropyl silyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2-{{[(4-methoxytrityl)thio]methylamino}-methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenyl acetate, isobutyrate, monosuccinoate, (E)-2-methyl-2-butenoate, o-(methoxycarbonyl)benzoate, .alpha.-naphthoate, nitrate, alkyl N,N,N',N'-tetramethylphosphorodiamidate, and 2-chlorobenzoate. In the case of sulfonates, sulfenates and sulfinates the protecting group for the OH can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, borate, and dimethylphosphinothiolyl. In the case of carbonates the protecting group for the OH can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH can be selected from dimethylthiocarbamate, N-phenylcarbamate, N-methyl-N-(o-nitrophenyl)carbamate. The mention of these groups should be not interpreted as a limitation of the scope of the invention, since they have been mentioned as a mere illustration of protecting groups for OH, but further groups comprising said function may be known by the skill person in the art, and they are to be understood to be also encompassed by the present disclosure.

An example of a method of producing a compound having a dihydropyran structure (first to twelfth steps) according to the present embodiment is shown in the following reaction formula (I). Hereinafter, an certain aspect of each step will be specifically described in the order of the first step to the twelfth step.

Reaction Formula (I)

[Chem. 3];

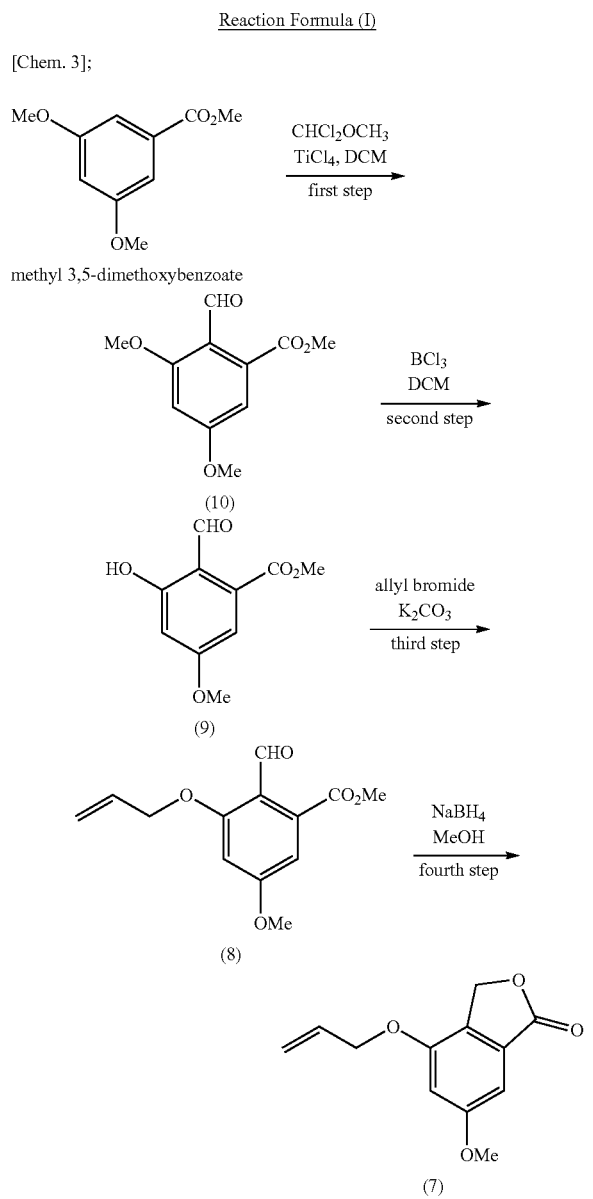 [SMILES: COC(=O)c1cc(OC)cc(OC)c1 ; COC(=O)c1cc(OC)cc(OC)c1C=O ; COC(=O)c1cc(OC)cc(O)c1C=O ; C=CCOc1cc(OC)cc(C(=O)OC)c1C=O ; C=CCOc1cc(OC)cc2c1COC2=O]

(1) The first step is performed according to the synthesis method described in the literature Hassall, C. H., Morgan, B. A. *J. Chem. Soc., Perkin Trans. 1*. 1973, 2853-2861.

Methyl 3,5-dimethoxybenzoate (2.90 g, 14.8 mmol) is dissolved in $CH_2Cl_2$ (60 mL), and $TiCl_4$ (2.80 mL, 25.5 mmol) is added thereto using a dropping funnel. Dichloromethyl methyl ether (1.80 mL, 20.0 mmol) is then added to the mixture while cooling the reaction solution at 0 deg C., and the mixture is stirred at room temperature for 25 min. Thereafter, 1.0 M aq.HCl (150 mL) is added and stirred, and then the organic layer is separated therefrom. The removed organic layer is washed with $H_2O$ (30 mL×3) and saturated brine (5 mL) and dried over $MgSO_4$ (dehydration). By distilling off the solvent under reduced pressure, a compound (3.21 g) represented by the formula (10) is obtained, which is used for the next reaction without purification.

(2) The second step is performed according to the synthesis method described in the literature Broadhust, M. J., Hassall, C. H., Thomas, G. J. *J. Chem. Soc., Perkin Trans. 1*. 1977, 2502-2512.

The compound represented by the formula (10) is dissolved in $CH_2Cl_2$ (30 mL), and $BCl_3$ (1.0 M in $CH_2Cl_2$, 21.5 mmol) is added thereto while cooling the reaction solution at 78 deg C. After stirring the mixture at room temperature for 2 hours, the reaction solution is poured into 1.0 M aq.HCl (80 mL) that cooled in an ice bath. The organic layer is separated therefrom, washed with $H_2O$ (30 mL×3) and brine (20 mL), and dried over $MgSO_4$. By distilling off the solvent under reduced pressure, a compound (2.95 g) represented by the formula (9) is obtained, which is used for the next reaction without purification.

(3) In the third step, the obtained compound (2.95 g) represented by the formula (9) is dissolved in acetone (90 mL), and $K_2CO_3$ (2.88 g, 21.1 mmol) and allyl bromide (1.80 mL, 21.1 mmol) are added thereto. The mixture is then heated to reflux for 3 hours and cooled down to room temperature. Next, $H_2O$ is added to the mixture until the precipitated solid is dissolved, and then the mixture is neutralized with 1 M aq.HCl. After acetone is distilled off, ethyl acetate (80 mL) is added thereto, and the organic layer is washed with $H_2O$ (20 mL×3) and brine (10 mL), and dried over $MgSO_4$. The solvent was distilled off under reduced pressure to obtain the compound (3.31 g) represented by the formula (8), which is used for the next reaction without purification.

(4) In the fourth step, the obtained compound (3.27 g) represented by the formula (8) is dissolved in MeOH (70 mL), and $NaBH_4$ (743 mg, 19.6 mmol) is added at 0 deg C. The mixture is then stirred at room temperature for 30 min. After neutralizing the mixture with 1 M aq.HCl, the precipitated solid is suction-filtered such that a compound (1.91 g, 8.69 mmol) represented by the formula (7) is obtained. Further, the filtrate is concentrated and extracted with ethyl acetate (30 mL×3). The organic layer thereof is then washed with $H_2O$ (10 mL) and brine (5 mL), dried over $MgSO_4$. After distilling off the solvent, the residue is separated therefrom by silica gel column chromatography (ethyl acetate/hexane=1/2), such that 0.594 g (2.70 mmol) of the compound represented by the formula (7) is further obtained. $^1H$ NMR ($CDCl_3$): δ 3.86 (3H, s), 4.60 (2H, dt, J=5.2, 1.6 Hz), 5.23 (2H, s), 5.34 (1H, dd, J=10.4, 1.2 Hz), 5.42 (1H, dd, J=17.2, 1.6 Hz), 6.03 (1H, m), 6.67 (1H, d, J=2.0 Hz), 6.94 (1H, d, J=2.0 Hz). $^{13}C$ NMR (100 MHz, $CDCl_3$): δ 55.9, 68.0, 69.2, 98.8, 105.8, 118.4, 128.0, 128.4, 132.1, 153.8, 162.3, 171.2. MS (FAB) m/z; 221 $[M+H]^+$.

[Chem. 4]

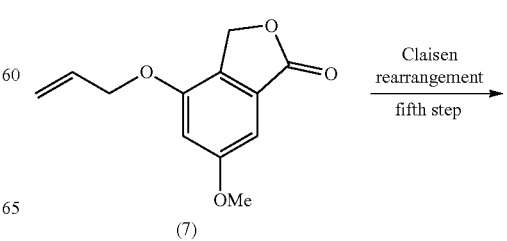

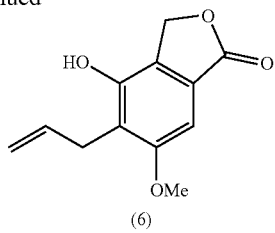

(6)

In the fifth step, the compound (1.23 g, 5.59 mmol) represented by the formula (7) is mixed with N,N-diethylaniline (0.1 mL), and heated at 220° C. for 1 hour under Ar atmosphere. After the mixture is cooled down to room temperature, the mixture is separated by silica gel column chromatography (ethyl acetate/hexane=1/2), 1.06 g (4.82 mmol, yield 86%) to obtain the compound represented by the formula (6). $^1$H NMR (CDCl$_3$): δ 3.57 (2H, d, J=6.0 Hz), 3.88 (3H, s), 5.20-5.24 (2H, m), 5.24 (2H, s), 5.62 (1H, s), 5.97 (1H, m), 7.00 (1H, s). $^{13}$C NMR (100 MHz, CDCl$_3$): δ 27.8, 56.2, 68.2, 98.8, 116.9, 119.9, 125.4, 127.1, 134.9, 149.9, 159.4, 171.9. MS (FAB) m/z; 221 [M+H]$^+$.

[Chem. 5]

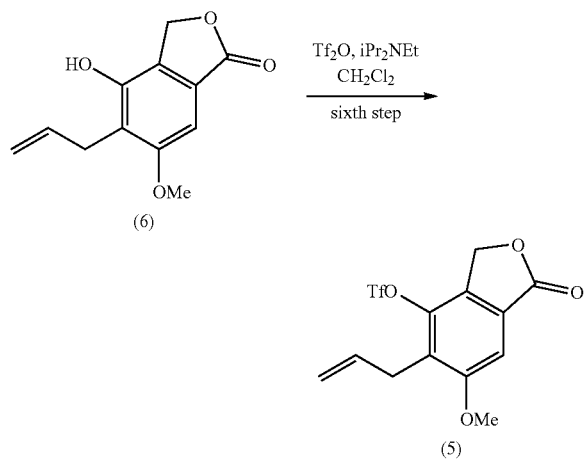

In the sixth step, the obtained compound represented by the formula (6) is dissolved in DCM (dichloromethane), and N,N-diisopropylethylamine (2.5 mL, 14.7 mmol) is added thereto. Further, trifluoromethanesulfonic anhydride (1.2 mL, 7.32 mmol) is dropped to the mixture under ice-cooling condition. After stirring the mixture for 1 hour under the ice-cooling condition, NaHCO$_3$(aq) is added to shift or change the mixture weakly basic, and the organic layer is separated. The aqueous layer is further extracted therefrom with CH$_2$Cl$_2$ (50 mL). The organic layer is collected, washed with H$_2$O (20 mL) and brine (10 mL), and dried over MgSO$_4$. After the solvent is distilled off under reduced pressure, the residue is separated and purified by silica gel column chromatography (ethyl acetate/hexane=1/2). As a result, 1.58 g (y.93%) of the compound represented by the formula (5) is obtained. $^1$H NMR (CDCl$_3$): δ 3.58 (2H, d, J=6.0 Hz), 3.96 (3H, s), 5.00-5.08 (2H, m), 5.36 (2H, s), 5.86 (1H, m), 7.40 (1H, s). $^{13}$C NMR (100 MHz, CDCl$_3$): δ 28.8, 56.7, 67.6, 106.3, 116.8, 118.4 (q, J=318 Hz), 127.1, 130.2, 131.0, 132.9, 140.7, 160.3, 169.4. MS (FAB) m/z; 353 [M+H]$^+$.

[Chem. 6]

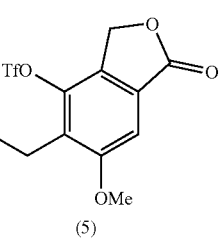

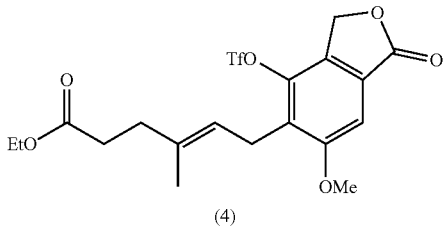

In the seventh step, the obtained compound (164 mg, 0.466 mmol) represented by the formula (5) is dissolved in Et$_2$O (3 mL), and ethyl 4-methyl-4-pentenoate (0.73 mL, 4.58 mmol) and Hoveyda-Grubbs 2$^{nd}$ cat. (28.8 mg, 0.046 mmol) are added thereto. The mixture is then heated under reflux for 32 hours, and the solvent is distilled off. The residue is separated therefrom and purified by silica gel column chromatography (ethyl acetate/hexane=1/3), such that 1.58 g (yield 41%, E:Z=3:1) of the compound represented by the formula (4) is obtained. $^1$H NMR (400 MHz): δ 1.19 (3H, t, J=7.2 Hz), 1.76 (3H, s), 2.25 to 2.40 (4H, m), 3.53 (2H, d, J=6.8 Hz), 3.95 (3H, s), 4.06 (2H, q, J=7.2 Hz), 5.10 (1H, t, J=6.8 Hz), 5.35 (2H, s), 7.38 (1H, s). $^{13}$C NMR (100 MHz) δ 14.1, 16.1, 24.1, 33.1, 34.6, 56.6, 60.2, 67.6, 106.3, 118.5 (q, J=320 Hz), 119.8, 126.7, 131.1, 131.7, 136.3, 140.5, 160.3, 169.5, 173.1. MS (DART) m/z; 467 [M+H]$^+$.

[Chem. 7]

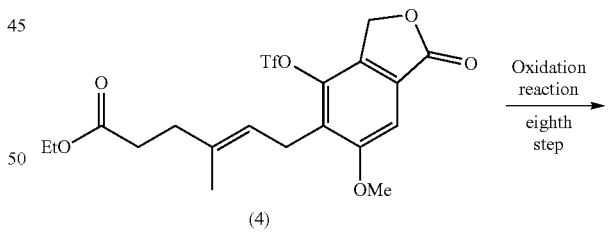

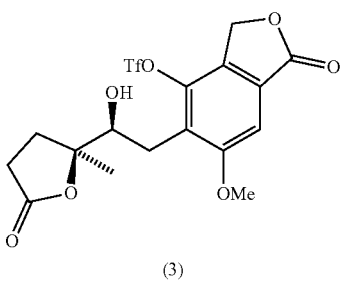

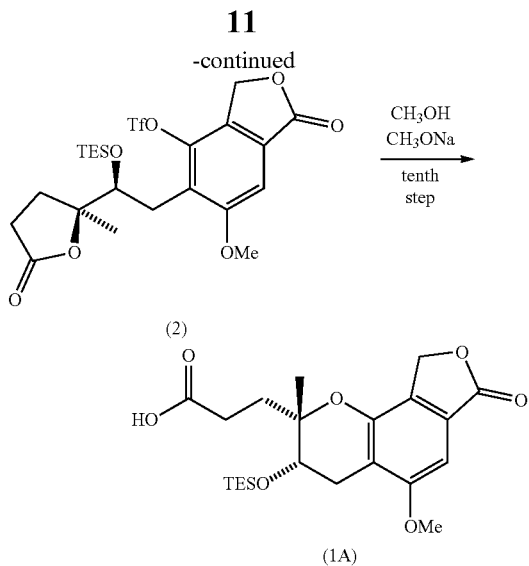

In the eighth step, the compound (107 mg, 0.230 mmol) represented by the formula (4) is dissolved in a mixed solvent of 0.4 mL of acetone and 0.05 mL of $H_2O$, and N-methylmorpholine N-oxide (54.0 mg, 0.462 mmol) and 4% $OsO_4$ aqueous solution (70 μL, 0.011 mmol) are subsequently added to the mixed solvent. The mixture is left at room temperature for 18 hours to react under the atmosphere. The reacted solution is added with $Na_2S_2O_4$ (10 mg) and Florisil (10 mg), diluted with 10 mL of acetone, and neutralized with dilute hydrochloric acid. Further, celite filtration is performed, and the filtrate is adjusted to pH 1 with 6N HCl sol. After extraction with ethyl acetate (10 mL×2), the organic layer is washed with brine (2 mL) and dried over $MgSO_4$. After the solvent is distilled off under reduced pressure, the residue is separated and purified by silica gel column chromatography (ethyl acetate/hexane=1), such that 77 mg (yield 74%, dr=3:1) of the compound represented by the formula (3) is obtained. $^1$H NMR (400 MHz) δ 1.50 (3H, s), 2.01 (1H, m), 2.43 (1H, m), 2.69 (2H, t, J=8.0 Hz), 3.09 (2H, m), 3.83 (1H, dd, J=8.8, 4.4 Hz), 3.99 (3H, s), 5.37 (2H, s), 7.44 (1H, s). $^{13}$C NMR (100 MHz) δ 21.6, 26.9, 29.1, 30.4, 57.0, 67.6, 75.6, 88.0, 106.4, 118.5 (q, J=319 Hz), 127.5, 128.9, 131.3, 141.4, 160.3, 169.2, 176.5. MS (DART) m/z; 455 [M+H]$^+$.

In the ninth step, the obtained compound (30 mg, 0.066 mmol) represented by the formula (3) is dissolved in $CH_2Cl_2$ (1.3 mL), and 2,6-lutidine (23 μl, 0.197 mmol) and triethylsilyl trifluoromethanesulfonate (22 μl, 0.097 mmol) are added thereto under ice-cooling condition, and the mixture is reacted for 4 hours. After adding $CH_2Cl_2$ (15 mL) thereto, the mixture is washed with $H_2O$ (3 mL×3) and brine (1 mL), and is dried over $MgSO_4$. After the solvent was distilled off under reduced pressure, the residue is separated and purified by silica gel column chromatography (ethyl acetate/hexane=2), such that 34 mg (yield 91%) of the compound represented by the formula (2) is obtained. $^1$H NMR (400 MHz) δ 0.22-0.38 (6H, m), 0.75 (9H, t, J=8.0 Hz), 1.43 (3H, s), 2.02 (1H, m), 2.21 (1H, m), 2.59 (1H, ddd, J=18.0, 9.6, 3.6 Hz), 2.71 (1H, m), 2.92 (2H, m), 3.98 (3H, s), 4.04 (1H, dd, J=7.2, 6.0 Hz), 5.29 (1H, d, J=15.6 Hz), 5.42 (1H, d, J=15.2 Hz), 7.42 (1H, s). $^{13}$C NMR (100 MHz) δ 4.6, 6.5, 19.7, 28.4, 29.0, 30.3, 56.8, 67.6, 76.3, 88.5, 106.2, 118.4 (q, J=318 Hz), 127.2, 129.2, 131.4, 141.6, 160.2, 169.3, 175.9. MS (DART) m/z; 569 [M+H]$^+$.

The tenth step includes at least the following reactions. That is, the obtained compound (24 mg, 0.042 mmol) represented by the formula (2) is dissolved in 1.0 mL of $CH_3OH$, and $CH_3ONa$ (28% in $CH_3OH$, 8.6 mg, 0.075 mmol) is added thereto under ice cooling condition. The mixture is then stirred for 2 hours. The mixture is neutralized with 1N HCl sol. and extracted with ethyl acetate (10 mL×2). The organic layer is washed with brine (2 mL), dried over $MgSO_4$. After the solvent is distilled off under reduced pressure, the residue is separated therefrom and purified by silica gel column chromatography (ethyl acetate/hexane=1), such that 17 mg (yield 93%) of the compound represented by the formula (1A) is obtained. $^1$H NMR (400 MHz) δ 0.59 (6H, q, J=7.6 Hz), 0.81 (9H, t, J=7.6 Hz), 1.40 (3H, s), 2.09 (1H, m), 2.17 (1H, m), 2.61 (1H, ddd, J=18.0, 6.0, 3.6 Hz), 2.67-2.79 (2H, m), 3.02 (1H, dd, J=10.4, 2.4 Hz), 3.88 (3H, s), 3.91 (1H, dd, J=10.0, 2.4 Hz), 5.23 (1H, d, J=15.2 Hz), 5.28 (1H, d, J=15.2 Hz), 6.99 (1H, s). $^{13}$C NMR (100 MHz) δ 4.5, 6.4, 19.1, 27.3, 28.9, 31.2, 56.3, 68.1, 80.0, 88.1, 98.6, 119.7, 126.1, 127.9, 151.0, 159.1, 171.5, 175. 5. MS (DART) m/z; 465 [M+H]$^+$.

Details of $^1$H NMR of the compound represented by the above formula (1A) are shown in FIG. 1. FIG. 1 clearly shows signals 1 to 8 that indicate characteristics of the compound represented by the formula (1A). This is an example showing a nuclear magnetic resonance spectrum of each proton, which is a feature of the compound having a dihydropyran structure of the present disclosure.

The eighth step to the tenth step of the present embodiment are not limited to the eighth step to the tenth step of the first embodiment described above. The eighth step to the tenth step of the first embodiment described above may be constituted by the following production step I.

[Chem. 8]

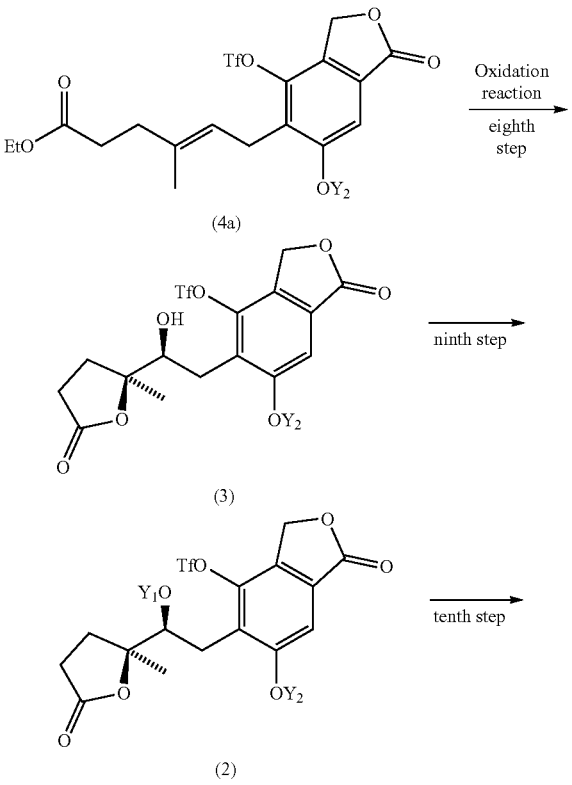

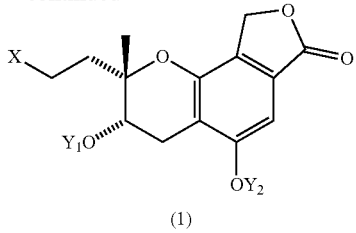

For example, the eighth step may be a step of obtaining the compound represented by the formula (3) by an oxidation reaction in which the compound represented by the formula (4a) is oxidized with an oxidizing agent that is selected from the group consisting of osmium tetroxide ($OsO_4$), cold alkaline potassium permanganate ($KMnO_4$), and performic acid ($HCO_2OH$).

Further, for example, the ninth step may be a step of obtaining the compound represented by the formula (2) by a reaction in which the compound represented by the formula (3) described above is substituted with a protecting group.

Further, for example, the tenth step may be a step of replacing the compound represented by the above formula (2) with a compound represented by the formula (1) comprising a functional group X composed of COOH, CHO, or —CH=C($CH_3$)—($CH_2$)$_2$—CH=C($CH_3$)$_2$ group.

Further, the tenth step may comprise a step of obtaining the compound represented by the formula (2) to synthesize a compound represented by formula (1B) and synthesize a compound represented by formula (1C).

[Chem. 9]

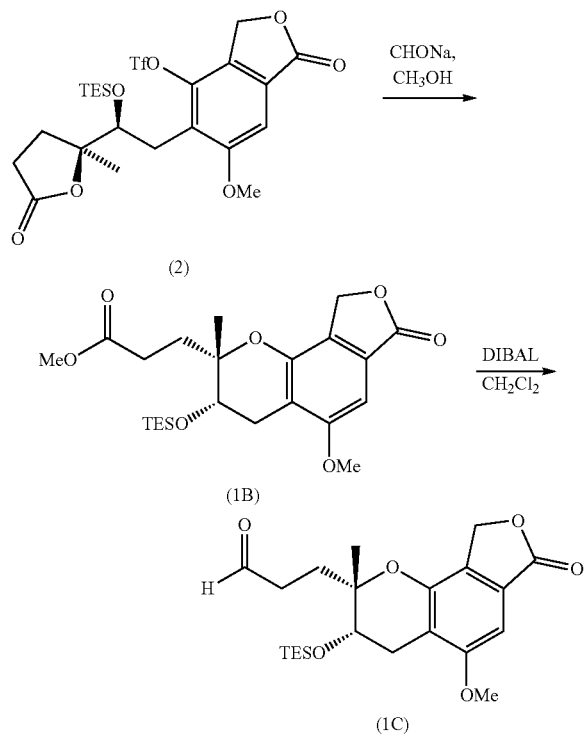

For example, in the reaction in which the compound represented by the formula (1A) is obtained from the compound represented by the formula (2), the compound represented by the formula (1B) may be achieved by applying anhydrous condition more strictly so as to prevent hydrolysis. Specifically, the compound represented by the formula (2) is dissolved in MeOH, and $CH_3ONa$ is added thereto, and stirred for several hours under ice cooling condition. After the mixture is neutralized with an appropriate HCl solution, the mixture is extracted with ethyl acetate, and the organic layer is washed with brine and dried over $MgSO_4$. The solvent is then distilled off under reduced pressure, and the residue is separated and purified by silica gel chromatography (dehydrated ethyl acetate/dehydrated hexane=1) to obtain the compound represented by the formula (1B).

Subsequently, the obtained compound represented by the formula (1B) is reduced using diisobutylaluminum hydride (DIBAL) to obtain the compound represented by the formula (1C) which is an aldehyde form.

Further, the tenth step may be a reaction step including a plurality of substitution reactions.

[Chem. 10]

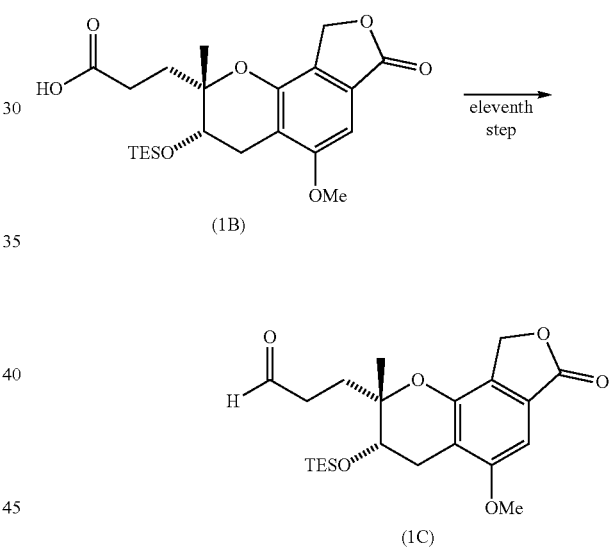

For example, the tenth step may comprise a reaction step including the eleventh step of synthesizing the compound represented by formula (1C) based on the compound represented by the formula (1A).

The eleventh step is a reaction step in which the compound represented by the formula (1A) is reacted with MeOH in the presence of a dehydrating agent consisting of a group containing a carbodiimide group such as 1-ethyl-3-(3-dimethylaminopropyl) carbodiimide hydrochloride and N,N'-dicyclohexylcarbodiimide and diisopropylcarbodiimide. The reacted solution is then reduced by using diisobutylaluminum hydride or lithium aluminum hydride as a reducing agent to obtain the compound represented by the formula (1C).

Further, the eleventh step may include two reaction steps, namely a step of synthesizing the compound represented by the formula (1B) and a step of synthesizing the compound represented by the formula (1C).

[Chem. 11]

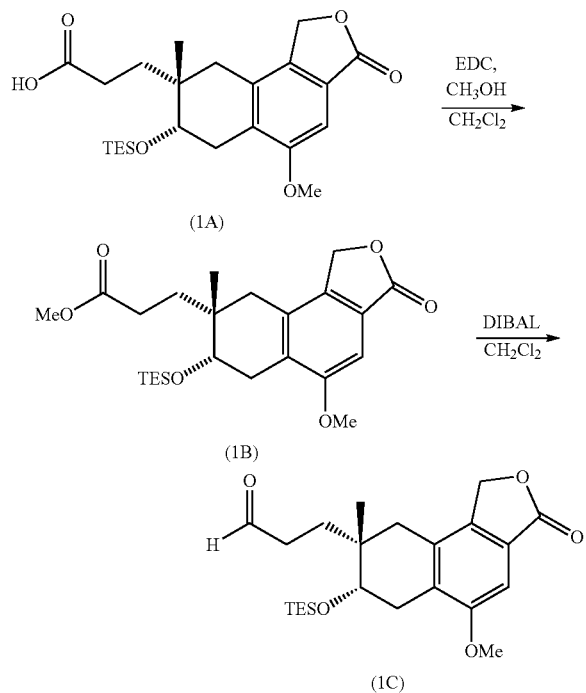

For example, the compound represented by the formula (1A) is reacted with MeOH in the presence of a dehydrating agent 1-ethyl-3-(3-dimethylaminopropyl) carbodiimide hydrochloride (EDC), and converted into the compound represented by the formula (1B) which is a methyl ester form.

Subsequently, the obtained compound represented by the formula (1B) is reduced using diisobutylaluminum hydride (DIBAL) to obtain a compound represented by the formula (1C) which is an aldehyde form.

[Chem. 12]

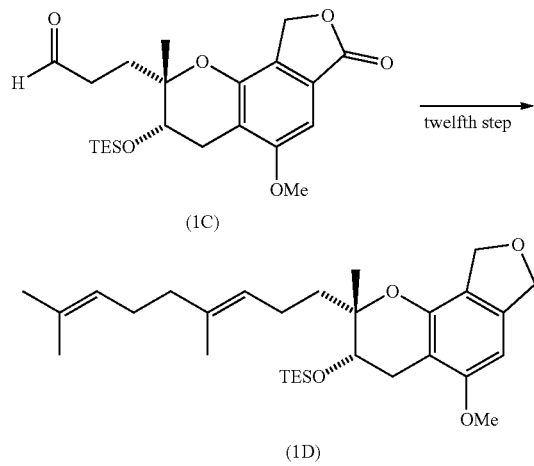

Further, the tenth step may include the twelfth step.

The twelfth step is an olefin synthesis method such as Takai-Lombard reaction, Takeda olefin synthesis, and Julia-Lithgo olefin synthesis.

The method of producing a compound having a dihydropyran structure of this disclosure is not limited to embodiment mentioned above. A step of purification using a known reaction method may also be included.

For example, the synthesis of the compound represented by the formula (1C) may include a reaction step in which the compound represented by the formula (1A) is hydrogenated in the presence of the ruthenium complex $RuCl_2(PPh_3)_3$ and the alkali metal salt $LiBPh_4$. In this case, the ruthenium complex is not limited to $RuCl_2(PPh_3)_3$. A group represented by the general formula $Ru_mX_nY_pZ_q$, wherein X is the same or different each representing a halogen atom, RCOO— (wherein R is an optionally substituted alkyl group or an optionally substituted aryl group), or β-diketonate; Y is a ligand containing one or more phosphorus atoms; Z is a ligand other than X and Y; m is an integer of 1 or more; n is an integer of 1 or more; p is an integer of 0 to 6; q is an integer from 0 to 2; the number of phosphorus atoms coordinated to the ruthenium atom is selected from the group of 2 to 10 times the ruthenium atom. The alkali metal salt is not limited to $LiBPh_4$. For example, $LiB(3,5-(CF_3)_2Ph)_4$, $NaBPh_4$, $NaB(3,5-(CF_3)_2Ph)_4$, $KBPh_4$, $KB(3,5-(CF_3)_2Ph)_4$, $CsBPh_4$, $CsB(3,5-(CF_3)_2Ph)_4$, LiOTs, NaOTs, KOTs, CsOTs, $LiNTf_2$, $NaNTf_2$, $KNTf_2$, $CsNTf_2$, LiOTf, NaOTf, KOTf, CsOTf, NaH, KH, CsH, Li(acac) (acac is acetylacetonato; same as below), Na(acac), K(acac), Cs(acac), LiOAc, NaOAc, KOAc, CsOAc, LiOH, NaOH, KOH, CsOH, Li(Ot-Bu) (t-Bu is tert Butyl group; same as below), Na(Ot-Bu), K(Ot-Bu), Cs(Ot-Bu) and the like. Further, the reducing agent is not limited to the group of the ruthenium complexes. It can also be selected from the group consisting of other effective transition complexes, lithium aluminum hydride, borane, sodium bis (2-methoxyethoxy) aluminum hydride, metallic sodium/ethanol, diisobutylaluminum hydride, sodium borohydride.

Further, the synthesis of the compound represented by the formula (1C) may include a reaction step in which pyridinium chlorochromate as an oxidizing agent is allowed to react on the compound after the compound represented by the formula (1B) is reduced and converted into an alcohol form. Here, the oxidizing agent is not limited to pyridinium chlorochromate, and is selected from, for example, the group consisting of pyridinium dichromate, and Dess-Martin oxidation.

Hereinafter, application examples of the chemical production method of Pre-SMTP and a group of SMTP will be described using the compound represented by the basic structural formula (1) which has a dihydropyran structure of the present disclosure as an intermediate.

That is, an application example in which the compounds represented by the formula (1), the formula (1B), the formula (1C) and the formula (1D) are used as intermediates will be described.

In the chemical production methods described below, most of the production steps starting from the compounds represented by the formula (1), the formula (1B), the formula (1C) and the formula (1D) are known and commonly used in this technical field. Thus, detailed description thereof is omitted.

Of course, needless to say that the method of producing the compounds represented by the formula (1A), the formula (1B), the formula (1C) and the formula (1D) of the present disclosure is the result of many years of extensive researches conducted by the inventors of the present disclosure. That is, the production method of the compound represented by the formula (1A), the formula (1B), the formula (1C) and the formula (1D) of the present disclosure is not easily obtained by a known production method.

Second Embodiment

The production method of Pre-SMTP of the second embodiment will be described. First, the thirteenth step will be described.

[Chem. 13]

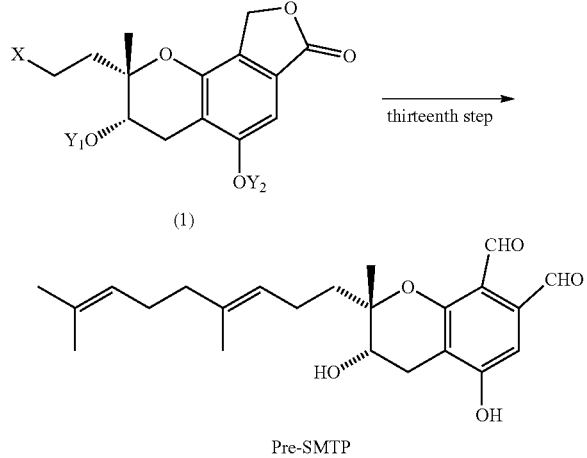

The thirteenth step is a production step mainly composed of a reduction reaction with a reducing agent, namely, a dialdehyde group formation reaction, a demethylation reaction, and a deTES protecting group reaction.

Here, a specific example of the reaction to reduce with a reducing agent, such as the dialdehyde group formation reaction, the demethylation reaction, and the de-TES protecting group reaction in the thirteenth step will be shown. That is, an example of each reaction step constituting the thirteenth step will be shown.

[Chem. 14]

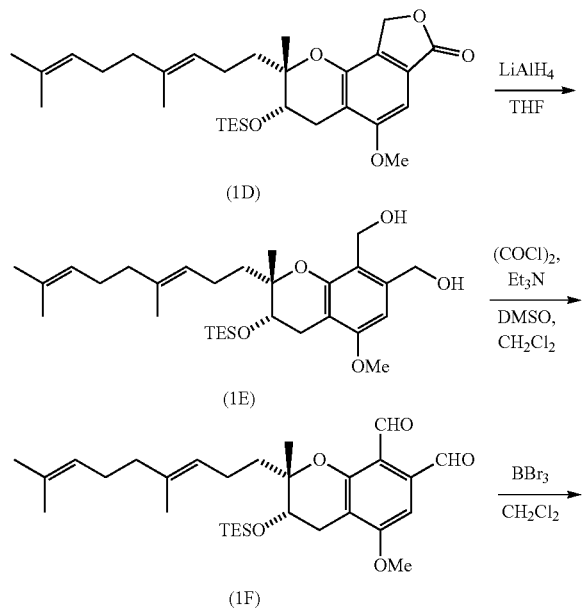

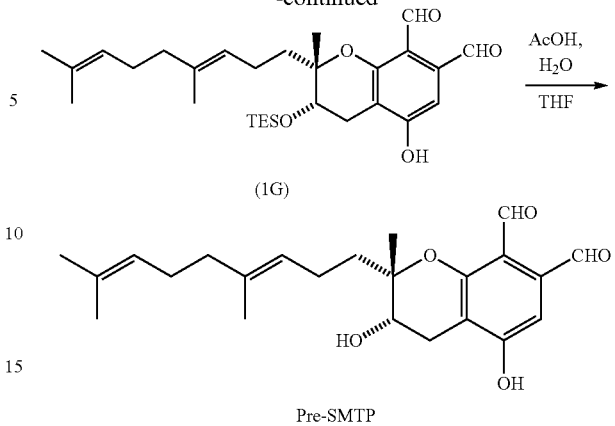

As the reaction step of reducing with a reducing agent, for example, the compound represented by the formula (1D) is reduced with $LiAlH_4$ to obtain the compound represented by the formula (1E) having a diol form.

Subsequently, as the dialdehyde group formation reaction, for example, the obtained compound represented by the formula (1E) is oxidized in Swern oxidation to obtain a compound represented by the formula (1F) which has a dialdehyde form.

Next, as the demethylation reaction, for example, the obtained compound represented by the formula (1F) is demethylated with $BBr_3$ to obtain the compound represented by the formula (1G).

Finally, as the de-TES protecting group reaction, for example, the Pre-SMTP is obtained by deprotection reaction of the TES group by hydrolysis in the acidic of the obtained compound represented by the formula (1G).

The reduction reactions, such as the dialdehyde group formation reaction, the demethylation reaction, and the de-TES protecting group reaction, are mainly known reactions. For example, the reducing agent may be selected from the group of lithium aluminum hydride, lithium borohydride, sodium borohydride, borane reduction, and the like. The dialdehyde group formation reaction may be selected from oxidation reactions, such as swarn oxidation, Fitzner Moffat oxidation, Albright Goldman oxidation, and Parrick-Dayling oxidation. The demethylation reaction and deTES protection may be known deprotection reactions.

Third Embodiment

Hereinafter, a chemical production step of a group of SMTP of the third embodiment will be described. The third embodiment includes the chemical production step of Pre-SMTP including the production step of the compound which has a dihydropyran structure or the chemical production step of Pre-SMTP starting from the above-mentioned intermediate which is a compound having a dihydropyran structure of the present disclosure.

That is, the third embodiment is a production method capable of obtaining a desired group of SMTPs, in which the Pre-SMTP obtained in the thirteenth step is added an amine compound selected from the group consisting of aminophenol, aminobenzoic acid, adenine, adenosine, aminodihydrophthalazinedione, aminonaphtholsulfonic acid, sulfanilic acid, and derivatives thereof.

Third Embodiment-1

The third embodiment-1 is a production method of SMTP-0. By adding ammonium acetate to the compound Pre-SMTP obtained in the thirteenth step under the absence of amine in buffer (20 mM potassium phosphate, pH7.4) or 50% aqueous acetone in the presence or absence of acetic acid (1%, v/v), Pre-SMTP is reduced and simultaneously SMTP-0 is formed.

Third Embodiment-2

The third embodiment-2 is a production method of SMTP-4. SMTP-4 is obtained by the reaction of the compound Pre-SMTP obtained in the thirteenth step with L-phenylalanine under the same conditions as in the third embodiment-1 (under the absence of amine in buffer (20 mM potassium phosphate, pH7.4) or 50% aqueous acetone in the presence or absence of acetic acid (1%, v/v)).

Third Embodiment-3

The third embodiment-3 is a production method of SMTP-6. SMTP-6 is obtained by the reaction of the compound Pre-SMTP obtained in the thirteenth step with L-tryptophan under the same conditions as in the third embodiment-1.

Third Embodiment-4

The third embodiment-4 is a production method of SMTP-54. SMTP-54 is obtained by the reaction of the compound Pre-SMTP obtained in the thirteenth step with L-glutamine under the same conditions as in the third embodiment-1.

Third Embodiment-5

The third embodiment-5 is a production method of SMTP-55. SMTP-55 is obtained by the reaction of the compound Pre-SMTP obtained in the thirteenth step with L-glutamic acid under the same conditions as in the third embodiment-1.

Third Embodiment-6

The third embodiment-6 is a production method of SMTP-7. SMTP-7 is obtained by the reaction of the compound Pre-SMTP obtained in the thirteenth step with Ornithine under the same conditions as in the third embodiment-1.

The production method of SMTP groups of the present disclosure is not limited to the third embodiment-1 to the third embodiment-6 described above. The application examples of the present disclosure comprise any chemical production method for a group of SMTPs which is the compound having a dihydropyran structure of the present disclosure as an intermediate. Or, the application examples of the present disclosure comprise any chemical production method for a group of SMTPs which comprises the step for producing a compound having a dihydropyran structure of the present disclosure.

In order to explain that the compound having the dihydropyran structure of the present disclosure or its production step is an important intermediate in the chemical production method for a group of SMTPs and Pre-SMTP, reverse synthesis analysis of SMTP-7 will be described.

Reverse synthesis analysis of SMTP-7

[Chem. 15]

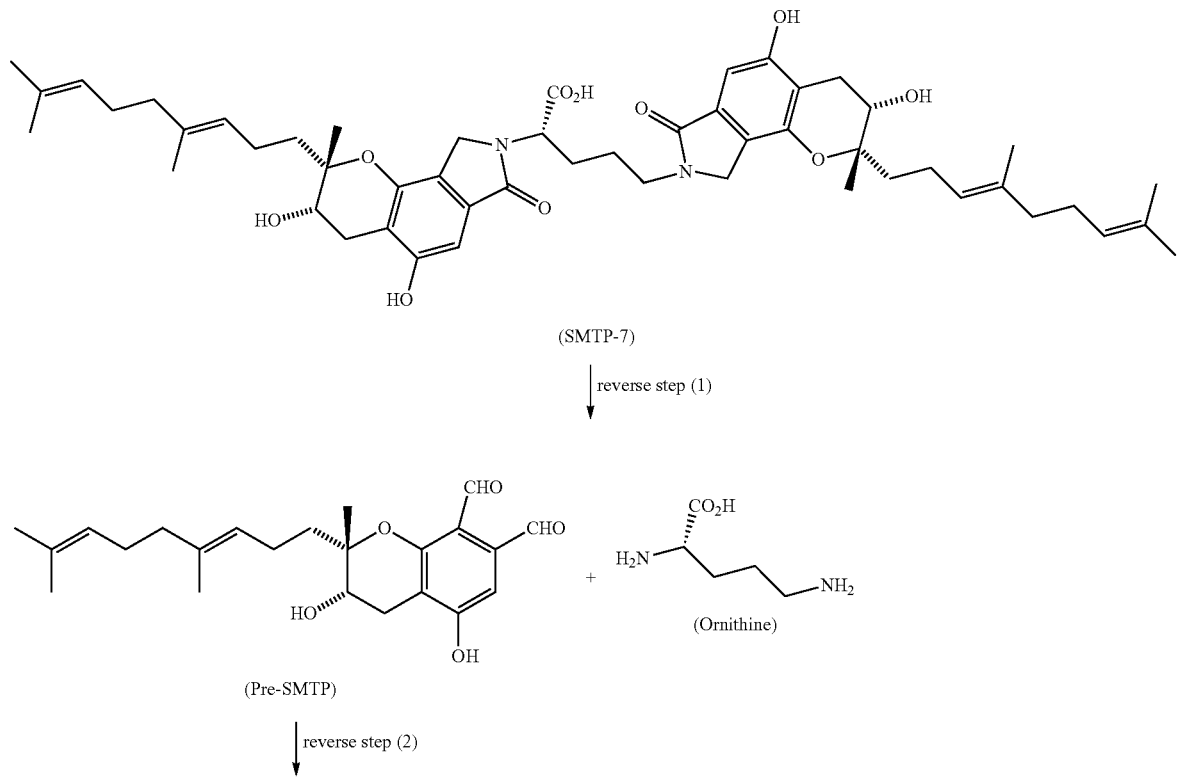

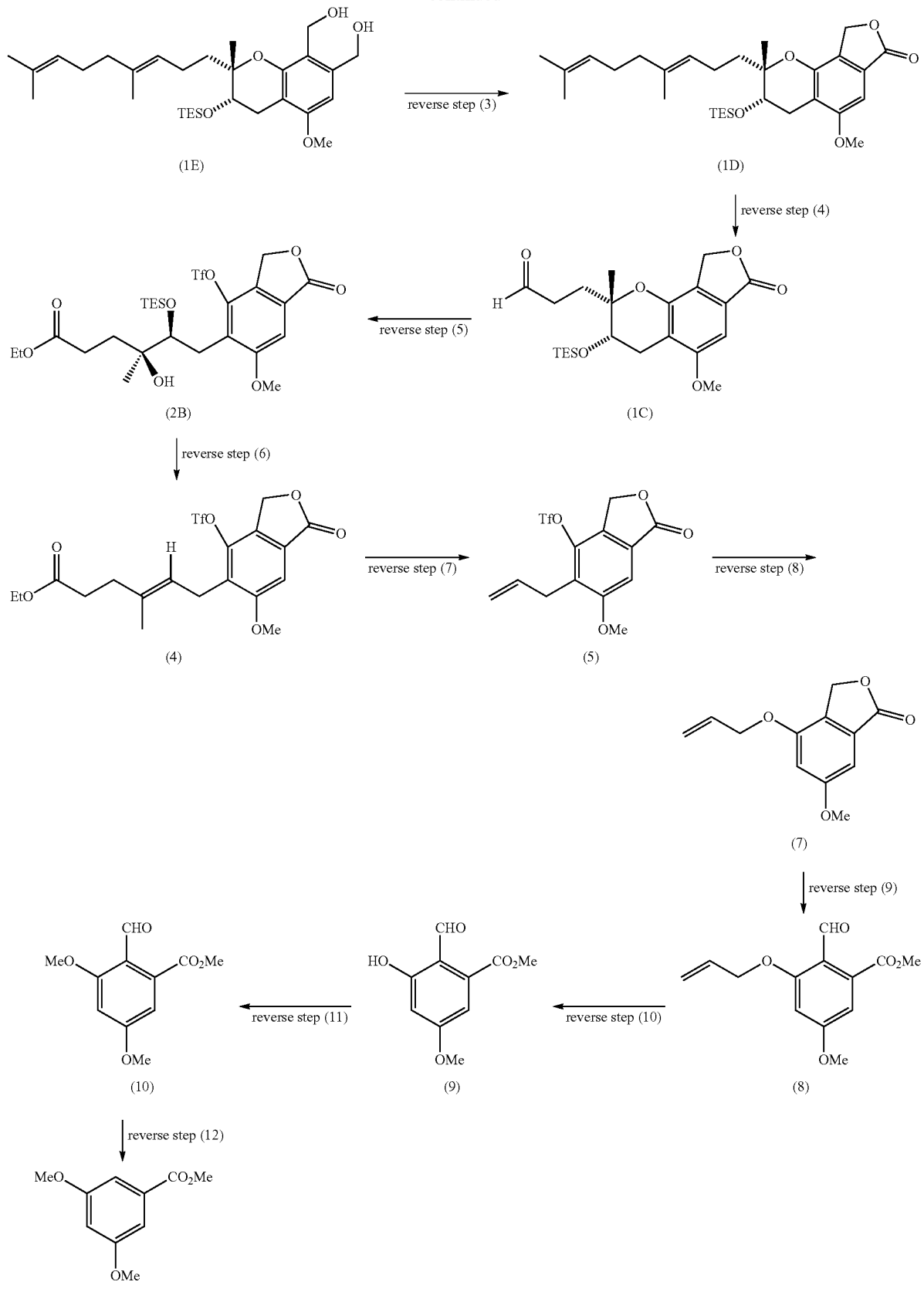

The present inventors have already described that the reverse reaction analysis was triggered by considering the chemical production method of a group of SMTPs. As an example, analyzes the reverse synthesis of SMTP-7 and theoretically study the synthesis route (production step). Based on the known knowledge, the present inventors estimated that the reverse synthesis (I) routes of SMTP-7 is the reverse step (1) to the reverse step (12). Among them, it can be seen that the reverse step (4) to the reverse step (12) correspond to the reverse reaction steps of the reaction from the first step to the tenth step of the present disclosure. Further, it is understood that the reverse step (5) and the reverse step (6) among the reverse step (4) to the reverse step (12) are very difficult to obtain by known knowledge in the field. It can be presumed that other reverse steps can be obtained stoichiometrically based on known knowledge in the art.

The reaction from reverse step (1) to reverse step (3) in the reverse synthesis of SMTP-7 will be described below.

The reverse step (1) is obtained by reacting Pre-SMTP with ornithine, that shows reverse step which when already known SMTP-7 decomposes, it becomes a precursor compound (Pre-SMTP) and ornithine.

Reverse Step (2)

[Chem. 17];

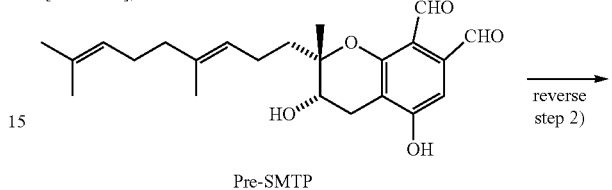

Reverse synthesis (I)

[Chem. 16]; Reverse Step (1)

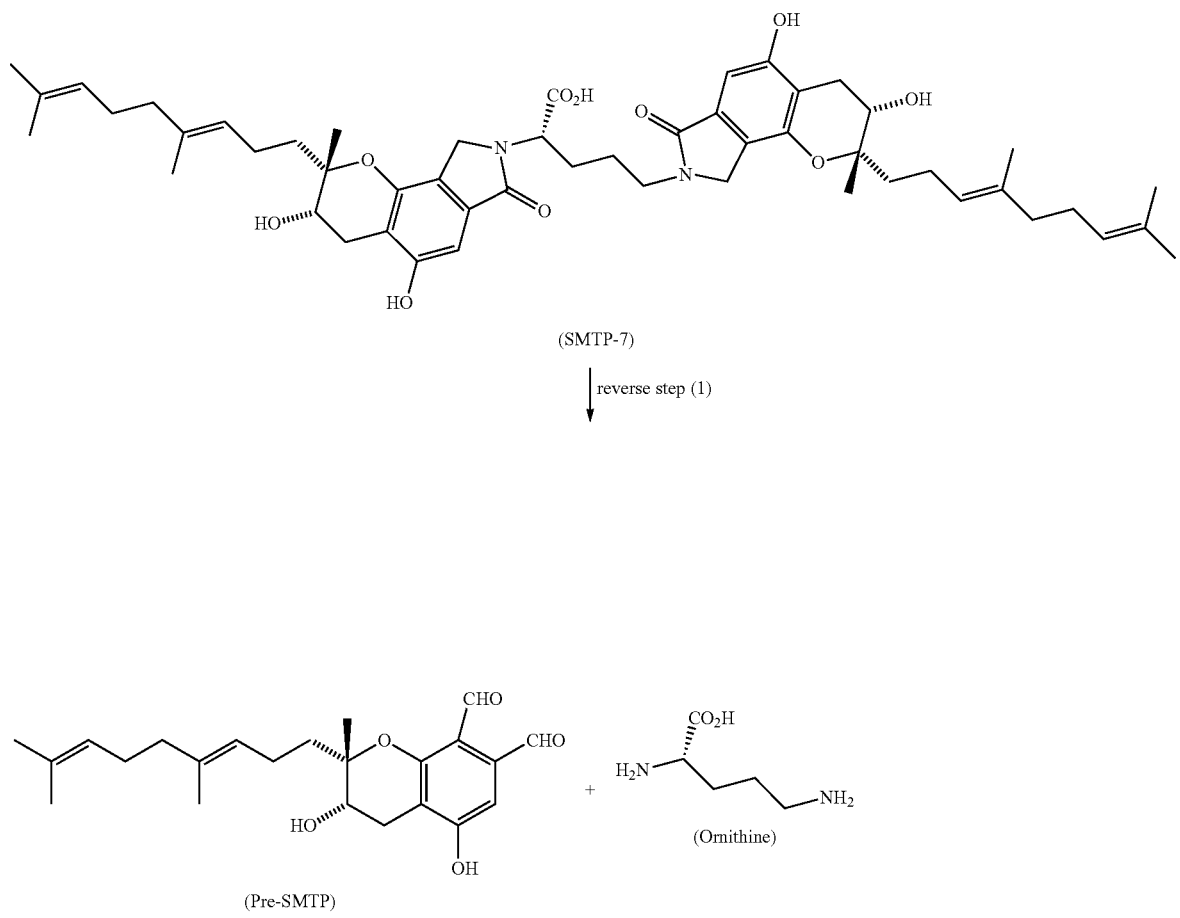

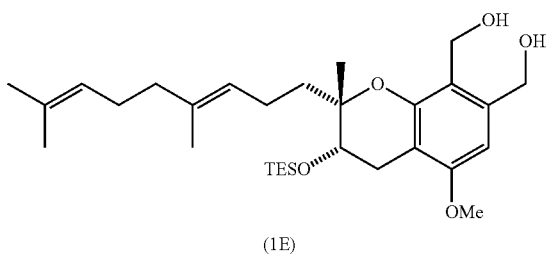

(1E)

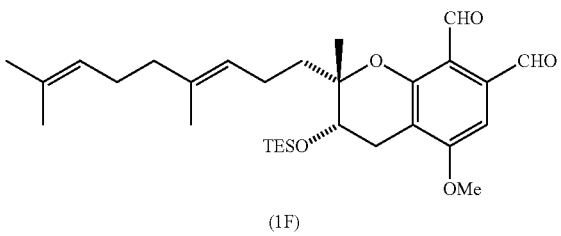

(1F)

In general, the reverse step (2) is considered to include three steps.

That is, the reverse step (2) comprises a step (1) and a step (2) and a step (3) in order to selectively convert Pre-SMTP into the compound represented by the formula (1E). The step (1) and step (2) protects a functional group that is not necessary for the reaction among a plurality of functional groups. In the step (3), a functional group necessary for the conversion (CHO site of Pre-SMTP) is selectively reacted.

For example, in the step (2), the compound represented by formula (1G) is dissolved in DMF, after added an equal amount of lithium carbonate, added an equal amount of iodomethane, and by reacted to obtain a compound represented by the formula (1F).

Here, the protecting group used in the reaction for protecting the unnecessary functional group of the present disclosure is not limited to those described above. For example, protecting groups include silyl-based protecting groups other than the TES protecting group, trimethylsilyl (TMS), triethylsilyl (TES), tert-butyldimethylsilyl (TBS or TBDMS), triisopropylsilyl (TIPS), tert-butyldiphenylsilyl (TBDPS) may be used, but further, may be an acyl protecting group or an acetal protecting group such as a methoxymethyl group (MOM), 2-tetrahydropyranyl group (THP), ethoxyethyl group (EE), etc may be used.

Step (1)

[Chem. 18];

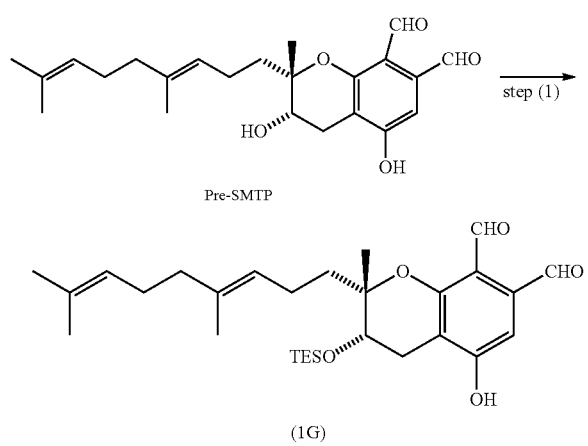

Step (3)

[Chem. 20];

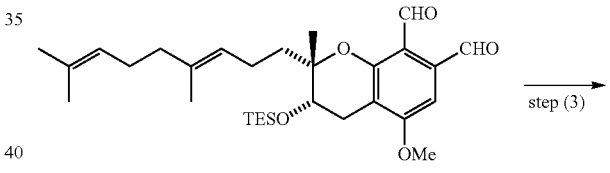

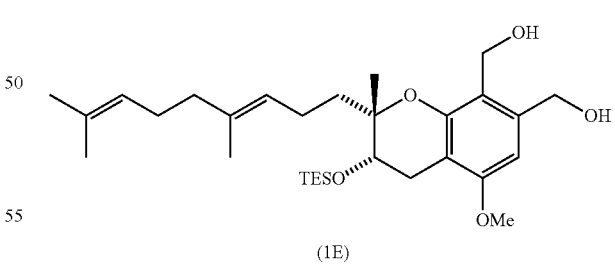

(1E)

For example, in the step (1), Pre-SMTP is dissolved in $CH_2Cl_2$, and added triethylsilyl trifluoromethanesulfonate (TES protecting group), reacted, washed with solvent, dehydrated with $MgSO_4$, solvent removed, by separation and purification by silica gel chromatography to can be obtain a compound represented by the formula (G).

Step (2)

[Chem. 19];

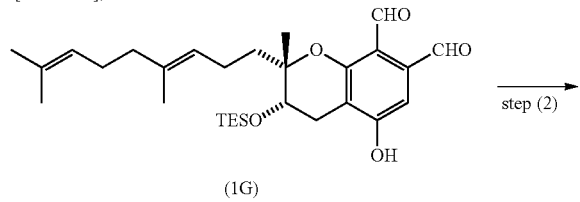

In step (3), for example, the compound represented by the formula (1E) is obtained by reducing the compound represented by the formula (1F) with $LiAlH_4$.

Here, the reducing agent is not limited to $LiAlH_4$. For example, it may be selected from the group consisting of borane, sodium bis (2-methoxyethoxy) aluminum hydride, metallic sodium/ethanol, diisobutylaluminum hydride, sodium borohydride, diisobutylaluminum hydride.

Reverse Step (3)

[Chem. 21];

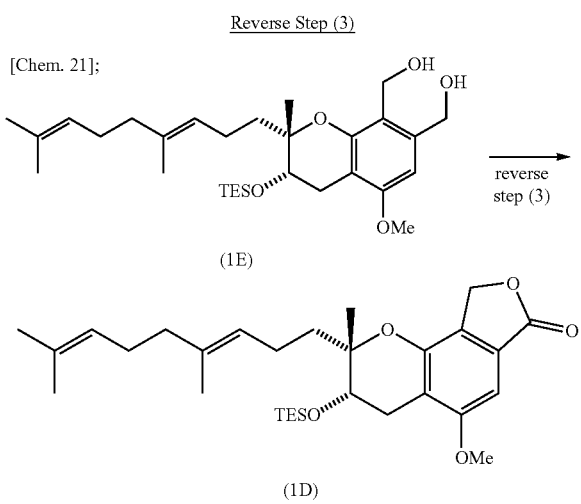

Many reaction paths are conceivable for the reverse step (3). For example, the compound represented by the formula (1E) is dehydrated to synthesizing a cyclic ether, and then oxidizing to obtain the compound represented by the formula (1D), It can be easily suggested to one skilled in the art.

In the reaction of the present disclosure, the solvent used is not particularly limited as long as it does not inhibit the reaction, For example, aliphatic hydrocarbons such as hexane, heptane and cyclohexane etc; ethers such as diethyl ether, diisopropyl ether, dimethoxyethane, cyclopentylmethyl ether and tetrahydrofuran; aromatic hydrocarbons such as toluene and xylene etc; alcohols such as methanol, ethanol and isopropyl alcohol and t-butyl alcoholetc; are exemplified. In addition, these solvents may be used individually or in mixture of 2 or more types.

Those skilled in the art can predict that the most difficult reverse synthesis route among the above-described reverse synthesis of SMTP-7 is the reverse step (5) and the reverse step (6). Therefore, the reverse step (5) and the reverse step (6) correspond to key production steps in the construction of a chemical production method for SMTP-7 or Pre-SMTP.

In the present disclosure, a chemical synthesis route of the first to thirteenth steps corresponding to the reversible synthesis route in the series of reverse steps described above was constructed. Among them, the synthesis method in the eighth to tenth steps of the reaction formula (I) of the present disclosure corresponds to the reaction route was considered to be the most difficult in the chemical production method of SMTP-7 and Pre-SMTP, and the compound represented by the basic formula (1) corresponds to the most important intermediate in the chemical production method of SMTP-7 and Pre-SMTP. That is, if the synthesis route in the eighth to tenth steps of the reaction formula (I) of the present disclosure or the compound represented by the basic formula (1) can be constructed, the chemistry production method of SMTP-7 and Pre-SMTP can be established. That is, for the first time, a chemical production method of SMTP-7 and Pre-SMTP is realized.

The compounds with dihydropyran structure of the present disclosure are not only intermediates that can be applied to the chemical production methods of Pre-SMTP and SMTP. The present disclosure can also be applied to a method of producing Pre-SMTP and a group of SMTP by a biological culture method using a compound having a dihydropyran structure as a starting material. Further, can also be applied to various production methods of Pre-SMTP and SMTP groups using each production step of the compound having a dihydropyran structure of the present disclosure (for example, Pre-SMTP combining a chemical production method and a biological culture method and a production method of a group of SMTP).

The compound having a dihydropyran structure of the present disclosure is also expected to function as a thrombolysis promoter. In this case, the thrombus dissolution promoter comprising as an active ingredient at least one compound having the dihydropyran structure.

The above-mentioned compound having a dihydropyran structure is expected to have an effective thrombolysis promoting action at a low molecular weight. In the thrombolytic agent, the compound having the dihydropyran structure can be contained in the thrombolytic agent in a form that is usually applicable as a pharmaceutical, such as a free form, a pharmaceutically acceptable salt, or an ester.

The dosage form of the thrombolytic agent containing the compound having a dihydropyran structure of the present disclosure can be appropriately changed depending on various administration forms. Examples of oral dosage forms include tablets, capsules, powders, fine granules, granules, solutions or syrups, etc. Examples of parenteral dosage forms include injections, drops, suppositories, inhalants, patches, etc. In order to maintain these forms, additives such as well-known solvents and excipients that can be used in these applications can be included.

The therapeutic pharmaceutical composition includes a compound having a dihydropyran structure of the present disclosure, pharmaceutically acceptable salts, derivatives, tautomers, prodrugs or stereoisomer thereof as an active ingredient.

The term "pharmaceutically acceptable salts, derivatives, prodrugs" refers to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

What is claimed is:

1. A method of producing a compound of formula (1), comprising a production step I, wherein the production step I is represented as:

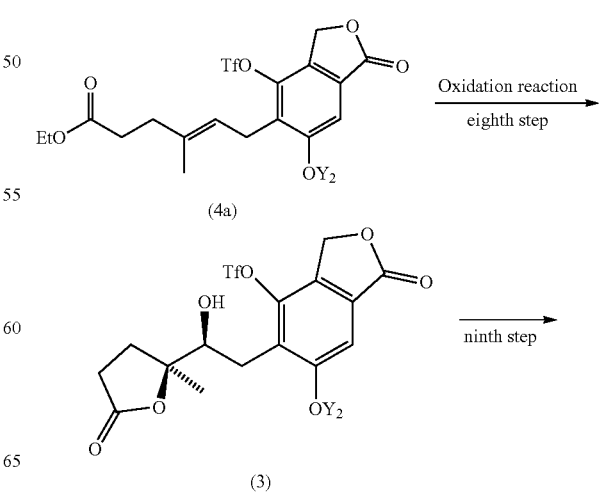

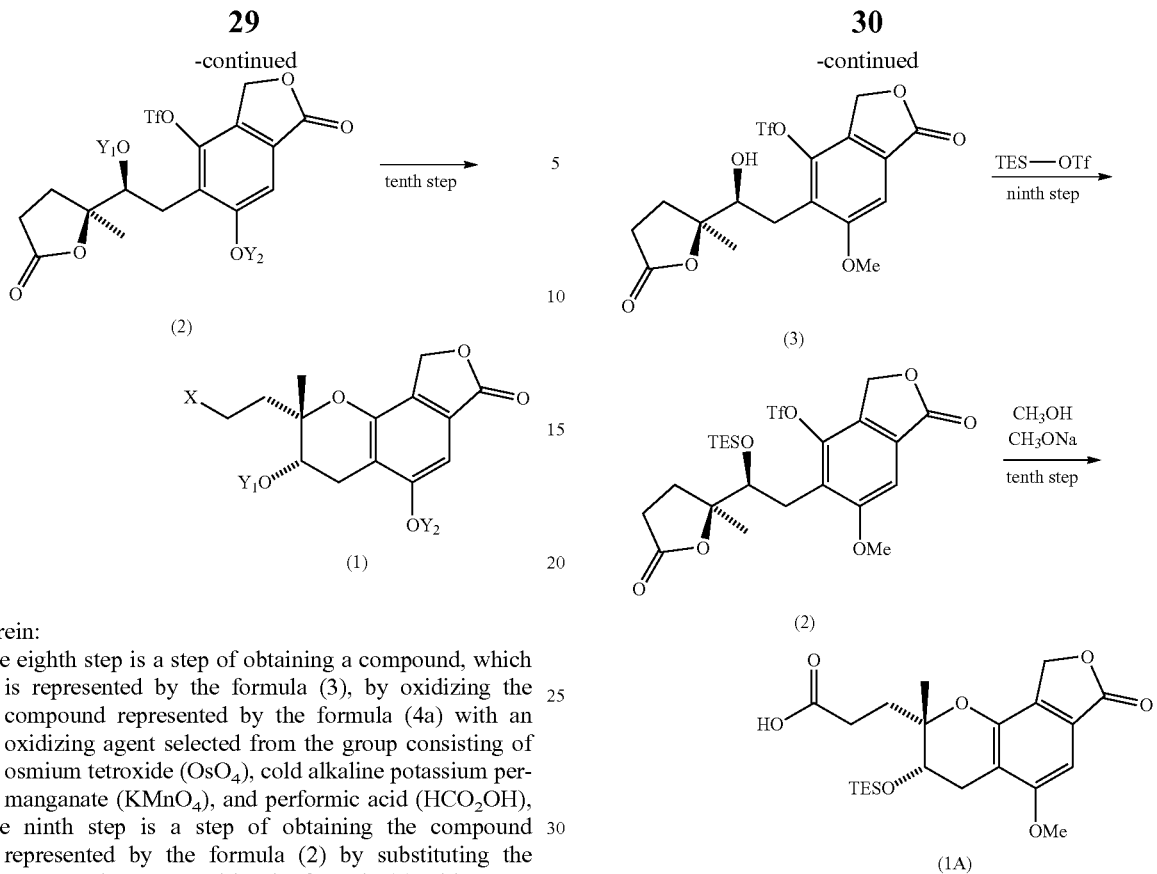

wherein:
the eighth step is a step of obtaining a compound, which is represented by the formula (3), by oxidizing the compound represented by the formula (4a) with an oxidizing agent selected from the group consisting of osmium tetroxide ($OsO_4$), cold alkaline potassium permanganate ($KMnO_4$), and performic acid ($HCO_2OH$),
the ninth step is a step of obtaining the compound represented by the formula (2) by substituting the compound represented by the formula (3) with a protecting group, and
the tenth step is a step of constructing a functional group X consisting of any one of COOH, CHO, and —CH=C($CH_3$)—($CH_2$)$_2$—CH=C($CH_3$)$_2$, and
wherein
$Y_1$ and $Y_2$ are each independently selected from the group consisting of trimethylsilyl, triethylsilyl (TES), triisopropylsilyl, t-butyldimethylsilyl, t-butyldiphenylsilyl or methyl, methoxymethyl, t-butyl, allyl, and benzyl.

2. The method according to claim 1,
wherein:
a compound represented by the following formula (4) is used as a starting material, and
in the tenth step, the compound represented by the formula (2) is dissolved in $CH_3OH$, and is stirred after being adding with $CH_3ONa$ under ice-cooling condition, a reaction product is extracted therefrom after neutralization, an organic layer of the extracted product is then washed with brine and dried with $MgSO_4$ to obtain a solvent, the solvent is then distilled off under reduced pressure, and the residue is separated and purified by silica gel chromatography,
wherein the production step I is a production step IA represented as:

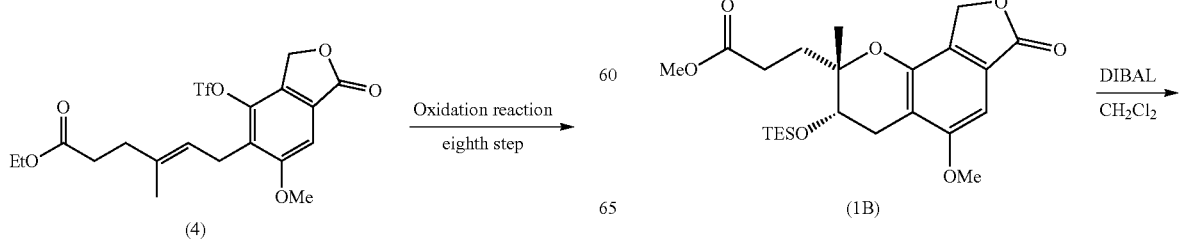

wherein $Y_1$ is TES and $Y_2$ is a methyl group.

3. The method according to claim 1, further comprising:
performing a reaction with the compound represented by the formula (2) under anhydrous conditions to obtain a compound represented by the following formula (1B), and
obtaining a compound represented by the following formula (1C) by reducing the obtained compound represented by the formula (1B) with a reducing agent

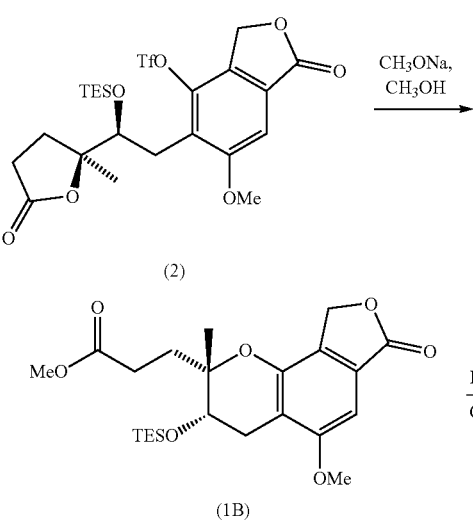

-continued

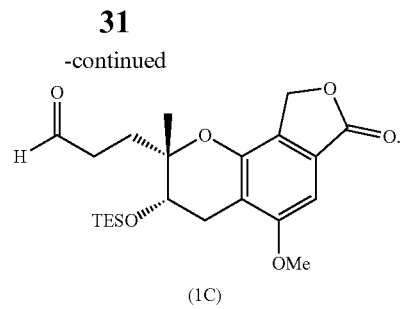

(1C)

4. The method according to claim 1, further comprising an eleventh step after the tenth step, wherein in the eleventh step the compound of formula (1) is the compound of formula (1A), and wherein the compound of formula (1A) is reacted with MeOH in the presence of a dehydrating agent, and reduced using a reducing agent:

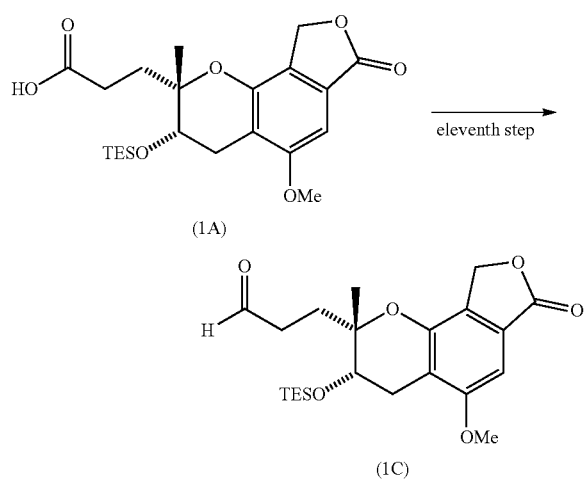

wherein: the dehydrating agent is a dehydrating condensing agent composed of a group containing a carbodiimide group selected from the group consisting of 1-ethyl-3-(3-dimethylaminopropyl) carbodiimide hydrochloride, N,N'-dicyclohexylcarbodiimide, and diisopropylcarbodiimide, wherein the reducing agent is diisobutylaluminum hydride or lithium aluminum hydride.

5. The method according to claim 1, further comprising a twelfth step of synthesizing the olefin after the tenth step, wherein in the twelfth step the compound of formula (1) is compound of formula (1C):

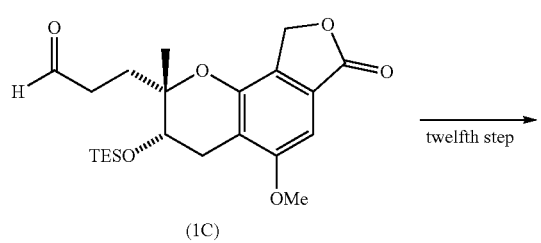

-continued

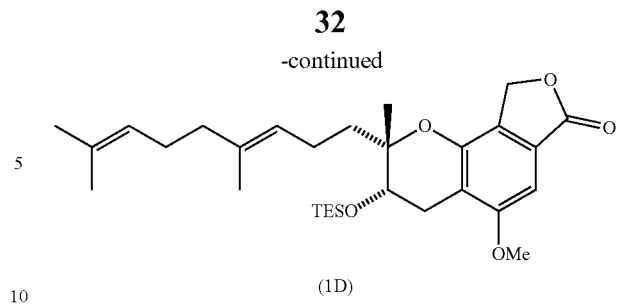

(1D)

wherein: the twelfth step is a reaction selected from the group consisting of a Takai-Lombard reaction, Takeda olefin synthesis, and Julia-Lithgo olefin synthesis.

6. The method according to claim 5, wherein the compound represented by formula (4a) is the compound of formula (4), wherein the compound of formula (4) is produced by a production step II comprising first to seventh steps, the production step II using methyl 3,5-dimethoxybenzoate as a starting material:

the production step II is represented as:

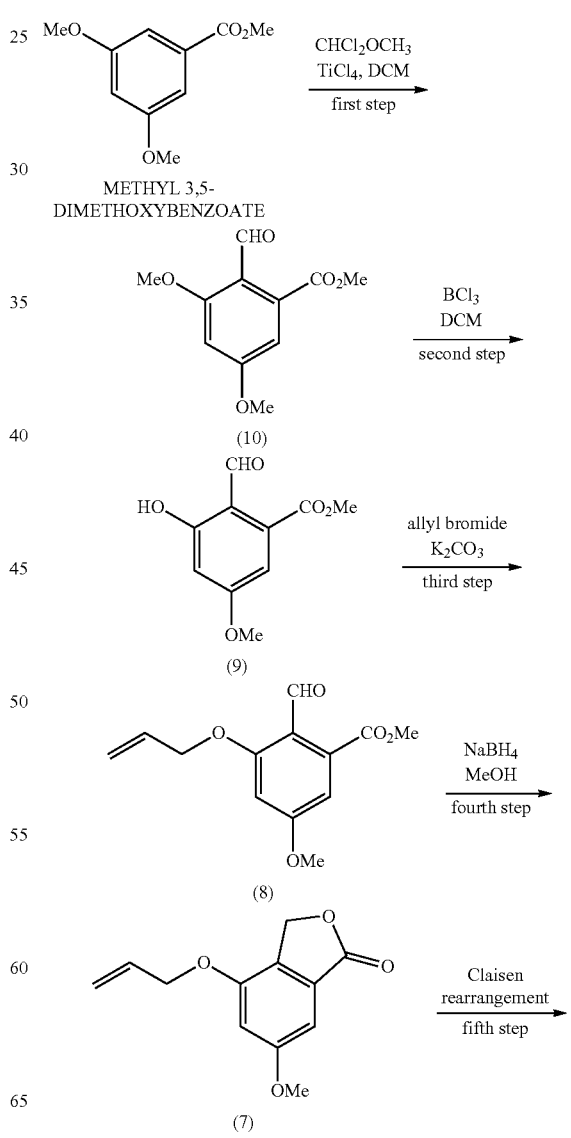

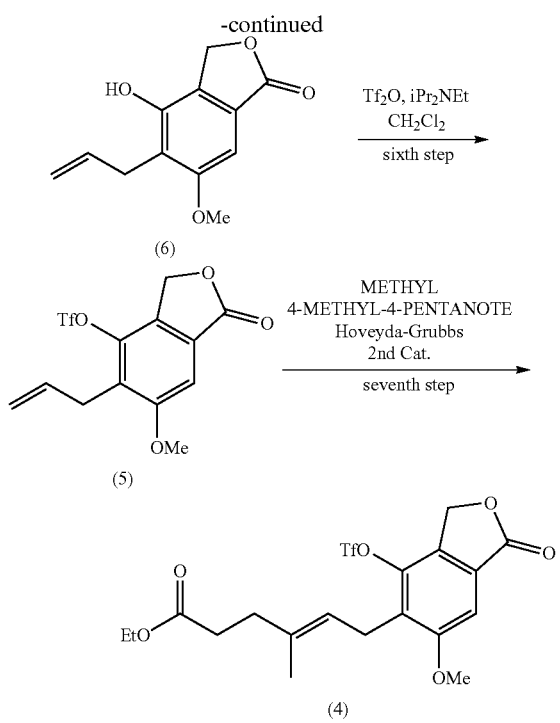

wherein:
(a) in the first step, methyl 3,5-dimethoxybenzoate is dissolved in CH$_2$Cl$_2$, and is added with TiCl$_4$ using a dropping funnel, the reaction solution is cooled, added with dichloromethyl methyl ether, and stirred at room temperature, the reaction solution is then added with HCl and stirred, an organic layer thereof is separated, washed, and dried, and the solvent is distilled off under reduced pressure to obtain the compound represented by the formula (10);
(b) in the second step, the obtained compound represented by the formula (10) is dissolved in CH$_2$Cl$_2$, and added with BCl$_3$ under cooling, the mixture is stirred at room temperature, the reaction solution is poured into chilled HCl, an organic layer thereof is separated therefrom, washed, and dried, and the solvent is distilled off under reduced pressure to obtain the compound represented by the formula (9);
(c) in the third step, the obtained compound represented by the formula (9) is dissolved in acetone and added with K$_2$CO$_3$ and allyl bromide, the mixture is heated to reflux, then returned to room temperature, and added with H$_2$O until a precipitated solid is dissolved, the reaction solution is then neutralized with HCl, acetone is distilled off from the reaction solution, ethyl acetate is then added thereto, an organic layer thereof is washed with H$_2$O and brine, and dehydrated, and the solvent is distilled off under reduced pressure to obtain the compound represented by the formula (8);
(d) in the fourth step, the obtained compound represented by the formula (8) is dissolved in MeOH, and added with NaBH$_4$ at low temperature, the mixture is stirred for 30 minutes at room temperature, and then neutralized with HCl, and a precipitated solid is suction filtered to obtain the compound represented by the formula (7);
(e) in the fifth step, the obtained compound represented by the formula (7) is mixed with N,N-diethylaniline, heated under an inert atmosphere, cooled down to room temperature, and the mixture is subjected to silica gel column chromatography (ethyl acetate/Hexane) to obtain the compound represented by the formula (6);
(f) in the sixth step, the obtained compound represented by the formula (6) is dissolved in DCM, added with N,N-Diisopropylethylamine, trifluoromethanesulfonic anhydride is dropped thereto and stirred under ice-cooling condition, the mixture is then added with aq.NaHCO$_3$ to shift the mixture weakly basic, an organic layer thereof is separated, the aqueous layer is further extracted with CH$_2$Cl$_2$, the organic layer is collected and washed with H$_2$O and brine, dehydrated, and the solvent is distilled off under reduced pressure, and the residue is separated and purified by silica gel column chromatography (ethyl acetate/hexane) to obtain the compound represented by the formula (5);
(g) in the seventh step, the obtained compound represented by the formula (5) is dissolved in Et$_2$O, added with ethyl 4-methyl-4-pentenoate and Hoveyda-Grubbs 2$^{nd}$ cat, the mixture is heated to reflux, the solvent is distilled off, and the residue is separated and purified by silica gel column chromatography (ethyl acetate/hexane) to obtain the compound represented by the formula (4).

7. The method of claim 5, wherein the compound of formula (1) is represented by the following formula (1B):

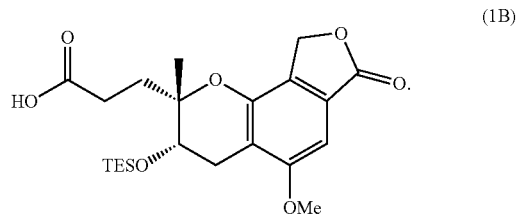

* * * * *